United States Patent [19]

Rapuano

[11] 3,995,372
[45] Dec. 7, 1976

[54] METHOD AND APPARATUS FOR SECURING A RETENTION PIN TO A TOOTH

[76] Inventor: Joseph A. Rapuano, 813 Morningside Road, Ridgewood, N.J. 07450

[22] Filed: Jan. 14, 1975

[21] Appl. No.: 540,770

[52] U.S. Cl. .................................. 32/40 R; 32/15
[51] Int. Cl.² .......................................... A61C 3/00
[58] Field of Search ............... 32/58, 40 R, 12, 15

[56] References Cited
UNITED STATES PATENTS

| | | | |
|---|---|---|---|
| 3,364,575 | 1/1968 | Baker | 32/15 |
| 3,863,345 | 2/1975 | Malmin | 32/57 |

*Primary Examiner*—Louis G. Mancene
*Assistant Examiner*—Jack Q. Lever
*Attorney, Agent, or Firm*—Albert H. Graddis; Frank S. Chow; George M. Yahwak

[57] ABSTRACT

This invention relates to a method for installing a friction lock retaining pin into a tooth through the use of ultrasonic vibrations and an apparatus by which conventional ultrasonic dental scalers may be adapted for use in this method.

7 Claims, 6 Drawing Figures

U.S. Patent  Dec. 7, 1976  3,995,372
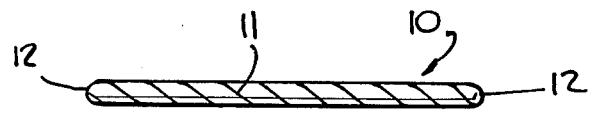
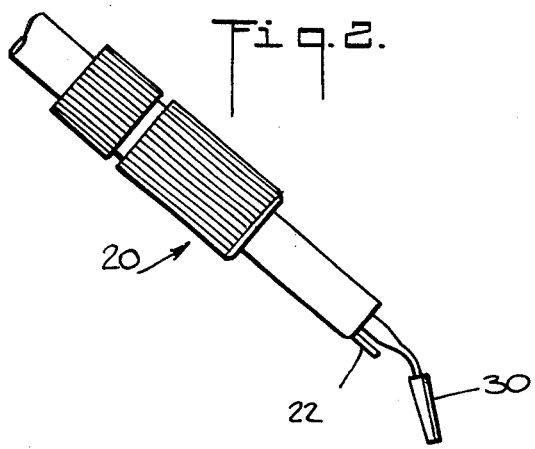
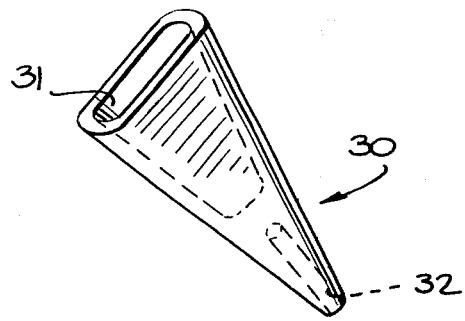
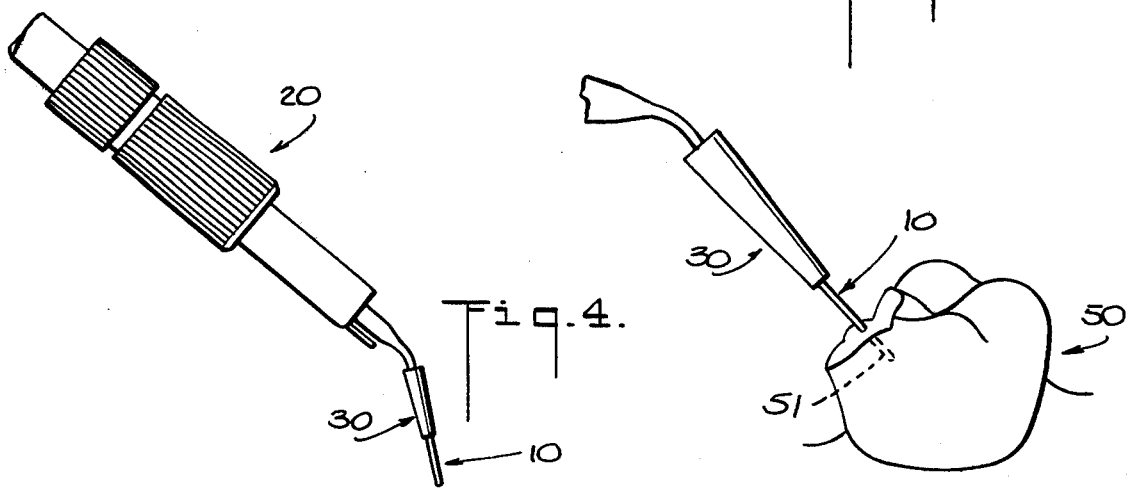
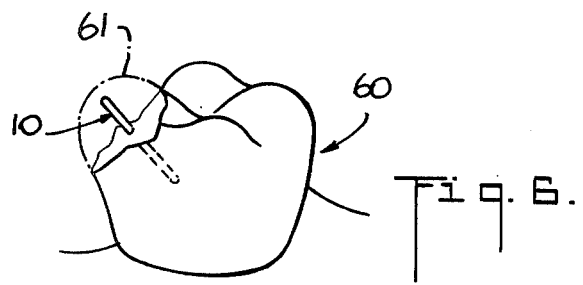

METHOD AND APPARATUS FOR SECURING A RETENTION PIN TO A TOOTH

Retention pins are widely used in the field of denistry to anchor a restoration material such as an amalgam, plastic, adaptic, composits, cements, or synthetic porcelain to a tooth which is being restored.

Restoration techniques concerning retention pins are used to repair fractured or broken teeth, as retainers for large fillings when there is insufficient tooth structure, and as retainers for building up the inner core of a tooth before crowning or capping. The tooth is prepared for restoration by conventional steps of cleaning and shaping the fracture or cavity. The pin or pins are then secured in the dentin portion of the tooth to act as the retainer for the restorative materials. The material is then packed, the retention pin or pins serving as an anchor and providing extra strength to the restored tooth.

Retention pins are secured to the injured tooth by cementing the pin into a previously drilled hole in the tooth, by friction locking a pin into the tooth, and by using self-threading pins wherein the pins are screwed into a previously made hole in the tooth.

In cementing techniques, a hole of a diameter considerably larger than that of the pin is drilled into the tooth; the hole is then filled with cement and the pin inserted. This method has several disadvantages. A relatively large hole is required and the drilling therefore must be done with care to avoid exposing the pulp canal of the tooth. Furthermore, dental cements are typically viscous and it is difficult to fill the hole with cement and insure that all entrapped air has been removed, and it also required extended chair time for the dentist and patient as the pin must be manually held in place by the dentist until this cement begins to set.

In the use of self-threading techniques, a hole of a diameter slightly smaller than that of the pin is drilled into the tooth, and the pin is screwed into the hole. This method also has several disadvantages, the most obvious being that the torque produced by screwing the pin into the hole may be great enough to crack the tooth. Another disadvantage is the difficulty in gaining access when screwing the pin in the posterior part of the mouth.

Under friction-locking techniques the retention pin is locked into place by friction when the pin is gently driven into a hole in the dentin of the tooth. The diameter of the hole is slightly smaller than the pin diameter, the difference conventionally being about 0.001 inch. If this method is done correctly, the dentin of the tooth is sufficiently resilient to expand around the pin as the pin is driven in place, and exert a contraction force on the pin gripping and clamping it in place. Of course this assumes that the driving force is correct to place the pin and that the area of the tooth to be restored is sufficiently exposed so as to allow sufficient room to hammer the pins and to fully seat them in the tooth.

I have now discovered that by using a novel adapter apparatus with conventional ultrasonic dental devices such as ultrasonic dental scaler units, it is possible to insert a retention pin into a tooth in such a manner that the disadvantages of the prior methods are overcome.

The invention may be more completely understood by reference to the drawings wherein:

FIG. 1 is a side view of a retention pin;
FIG. 2 is a view of a conventional scaler head unit and adapter;
FIG. 3 is a planar view of the adapter;
FIG. 4 is a view of the conventional head, adapter, and retention pin;
FIG. 5 is a perspective view of a retention pin being installed in a tooth; and
FIG. 6 is a perspective view of the retention pin installed in a tooth.

Referring to FIG. 1, a retention pin 10 is formed from a straight length of round wire which is preferably a corrosion-resistant material such as stainless steel. The pin is cut to a convenient length, and conventionally has a diameter of about 0.022 inches.

In a preferred form, a shallow spiral groove or scratch 11 is made in the surface of the pin. This spiral groove or scratch improves the adherence of a restoration material which is to be applied to the tooth around the pin, and also provides a venting path for air to escape from the hole as the pin is vibrated into place.

Preferably, each end 12 of the pin is rounded to eliminate burrs and to simplify insertion of the pin in a hole drilled in the tooth.

Referring to FIG. 3, an oval, generally cone shaped adapter 30 is shown having an opening 31 in the base of the cone capable of receiving and frictionally holding the scaler tip of a conventional ultrasonic dental scaler unit. It is of course possible and within the scope of this invention that the tip itself may be so modified to include the necessary properties of the adapter. At the apex of the adapter is a central hole 32 extending part way into the adapter along its longitudinal axis. Hole 32 is slightly larger than the diameter of pin 10 and receives pin 10 in a weak friction-fit yet capable of holding the pin in the adapter. The adapter 30 may be made of any material capable of use such as various plastics or metals; it may be magnetized also so that it is more strongly retained upon the scaler tip and in turn the retention pin is more strongly held.

Having thus described the adapter, it can more easily be seen in FIG. 2 how the adapter 30 is merely slipped over the scaling tip of a conventional scaler head 20. A tube 22 protrudes from each conventional head which delivers a water spray to the working zone when the unit is operating so that the tooth will not overheat.

As shown in FIG. 4, the retention pin 10 is merely slipped into the adapter 30 which is then attached to the head 20.

The head 20 is, as previously disclosed, part of conventional dental scaling machines. These are well known in the dental art and include, among others, Dentsply-Cavitron units manufactured by Dentsply International, 40K Ritterton Ultrasonic Scalers manufactured by Sybron Corporation, Sonus units manufactured by Litton Industries, and the Alph-Sonic units manufactured by Johnson and Johnson.

The method of installing the retention pin in a tooth is shown in FIG. 6. A tooth 50 having an injured portion is prepared for restoration following conventional denistry procedures. A hole 51 is drilled into a dentin zone of the tooth, and is usually oriented parallel to a pulp canal of the tooth. The hole in the dentin is slightly smaller than the diameter of the retention pin which is to be installed in the tooth.

One end of a retention pin 10 is inserted in the adapter 30, and the other end of the pin is positioned in the mouth of hole 51. The unit is then turned on and the pin is vibrated into the hole by gentle pressure and the vibrations of the ultrasonic generator. The ultrasonic vibrations vary between about 18,000 to about 40,000 cycles per second and are functions of the conventional unit's generator and transducer. Seating of the pin in the bottom of the hole is easily detected by the dentist. The adapter is then slipped off the pin which is now securely anchored in the tooth dentin. If the portion of the pin extending from the dentin is too long, it may be shortened or may also be bent after installation if desired.

Restoration of the tooth is then completed by packing a restoration material 61 around the retention pin.

The retention-pin installation method of this invention provides a very secure and precise mounting of the pin in the tooth. This secure mounting is due to the resilient nature of the dentin which allows the pin to be gently and precisely vibrated into place in an undersized hole. Once the pin is installed, the resilient dentin exerts a high pressure on the pin, gripping and securing it tightly in place.

I claim:

1. A device for inserting a dental retention pin into a tooth comprising:
   A generally conical body having a base and a truncated apex, the base and apex being located at opposite ends of the longitudinal axis of the body;
   Ultrasonic receiving means in said base wherein the base is connectible by a friction fit to a source of ultrasonic vibrations;
   Dental retention pin gripping means in said truncated apex of sufficient diameter to grip a dental retention pin during the insertion of the pin into a tooth.

2. The device of claim 1 which is unitary with an ultrasonic dental scaling tip.

3. The device of claim 1 which is magnetized.

4. The device of claim 1 wherein the means in said base comprise a hole adapted to tightly fit over an ultrasonic dental scaling tip.

5. The device of claim 1 wherein the gripping means at the apex comprises a cylindrical hole of sufficient diameter to accept the dental retention pin and extending into the body along its longitudinal axis.

6. A method for securing an elongated dental retention pin to a tooth by ultrasonic activity on the pin which comprises:
   Drilling a hole in a dentin zone of the tooth, the hole diameter being slightly less than the diameter of the retention pin;
   Placing an elongated dental retention pin into the gripping means of a device comprising a generally connical body having a base and a truncated apex, the base and apex being located at opposite ends of the longitudinal axis of the body, ultrasonic receiving means in said base having attached thereto a source of ultrasonic vibrations, and dental retention pin gripping means in said truncated apex of sufficient diameter to grip and hold a dental retention pin during the insertion of the pin into a tooth; and
   Driving the pin into the hole by application on the pin of an ultrasonic vibration while gently positioning the pin into the dentin zone of the tooth.

7. A method of restoring an injured tooth comprising the steps of drilling a hole in a dentin zone of the tooth, the hole diameter being slightly less than the diameter of an elongated dental retention pin;
   Placing an elongated dental retention pin into the gripping means of a device comprising a body having a base and apex, the base and apex being located at opposite ends of the longitudinal axis of the body, ultrasonic receiving means in said base having attached thereto a source of ultrasonic vibrations, and dental retention pin gripping means in said apex of sufficient diameter to grip and hold a dental retention pin during the insertion of the pin into a tooth;
   driving the pin into the hole by application on the pin of an ultrasonic vibration while gently positioning the pin into the dentin zone of the tooth; and
   applying a restoration material to the tooth around the retention pin.

* * * * *